United States Patent
Wrolstad et al.

(10) Patent No.: US 11,224,407 B2
(45) Date of Patent: Jan. 18, 2022

(54) CONDUCTIVE SUPPORT MEMBER FOR INTRAVASCULAR IMAGING DEVICE AND ASSOCIATED DEVICES, SYSTEMS, AND METHODS

(71) Applicant: KONINKLIJKE PHILIPS N.V., Eindhoven (NL)

(72) Inventors: David Kenneth Wrolstad, Fallbrook, CA (US); Maritess Minas, San Diego, CA (US); Princeton Saroha, Ladera Ranch, CA (US); Jeremy Stigall, Carlsbad, CA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 418 days.

(21) Appl. No.: 16/088,250

(22) PCT Filed: Mar. 30, 2017

(86) PCT No.: PCT/EP2017/057558
§ 371 (c)(1),
(2) Date: Sep. 25, 2018

(87) PCT Pub. No.: WO2017/167886
PCT Pub. Date: Oct. 5, 2017

(65) Prior Publication Data
US 2020/0330071 A1    Oct. 22, 2020

Related U.S. Application Data

(60) Provisional application No. 62/315,421, filed on Mar. 30, 2016.

(51) Int. Cl.
A61B 8/00    (2006.01)
A61B 8/08    (2006.01)
(Continued)

(52) U.S. Cl.
CPC .......... *A61B 8/445* (2013.01); *A61B 8/0891* (2013.01); *A61B 1/0011* (2013.01);
(Continued)

(58) Field of Classification Search
CPC .. A61B 8/12; A61B 8/54; A61B 8/445; A61B 8/0891; A61B 1/0011; A61B 1/00124; H05K 1/189
See application file for complete search history.

(56) References Cited

U.S. PATENT DOCUMENTS 4,917,097 A * 4/1990 Proudian ............ A61B 8/12
600/463
5,368,037 A  11/1994 Eberle
(Continued)

FOREIGN PATENT DOCUMENTS

WO    9723865 A1    7/1997

*Primary Examiner* — Boniface N Nganga

(57) ABSTRACT

An intravascular imaging device is provided. In one embodiment, the intravascular imaging device includes a flexible elongate member sized and shaped for insertion into a vessel of a patient, the flexible elongate member having a proximal portion and a distal portion; an imaging assembly disposed at the distal portion of the flexible elongate member, the imaging assembly including: a flex circuit; a conductor extending along the flexible elongate member and in electrical communication with the flex circuit; and a support member around which the flex circuit is positioned, the support member including a conductive portion electrically coupled to the support member.

20 Claims, 9 Drawing Sheets

(51) Int. Cl.
*A61B 1/00* (2006.01)
*A61B 8/12* (2006.01)
*H05K 1/18* (2006.01)

(52) U.S. Cl.
CPC ............ *A61B 1/00124* (2013.01); *A61B 8/12* (2013.01); *A61B 8/54* (2013.01); *H05K 1/189* (2013.01)

(56) References Cited

U.S. PATENT DOCUMENTS

| | | | |
|---|---|---|---|
| 5,779,644 A * | 7/1998 | Eberle | A61B 8/06 |
| | | | 29/25.35 |
| 6,780,157 B2 * | 8/2004 | Stephens | A61B 8/12 |
| | | | 600/437 |
| 2014/0182100 A1 * | 7/2014 | Reiter | H01L 41/338 |
| | | | 29/25.35 |
| 2014/0187960 A1 | 7/2014 | Corl | |
| 2014/0276085 A1 * | 9/2014 | Miller | A61B 8/483 |
| | | | 600/467 |
| 2015/0305710 A1 | 10/2015 | Stigall et al. | |
| 2015/0305716 A1 | 10/2015 | Rice et al. | |
| 2016/0081657 A1 | 3/2016 | Rice | |

\* cited by examiner

CONDUCTIVE SUPPORT MEMBER FOR INTRAVASCULAR IMAGING DEVICE AND ASSOCIATED DEVICES, SYSTEMS, AND METHODS

This application is the U.S. National Phase application under 35 U.S.C. § 371 of International Application No. PCT/EP2017/057558, filed on Mar. 30, 2017, which claims the benefit of Provisional Application Ser. No. 62/315,421, filed Mar. 30, 2016. These applications are hereby incorporated by reference herein.

TECHNICAL FIELD

The present disclosure relates generally to intravascular ultrasound (IVUS) imaging and, in particular, to the structure of an intravascular imaging device. For example, the structure can include a distal support member having a conductive portion that facilitates communication of electrical signals between a conductor and a flex circuit of the intravascular imaging device.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

Manufacturing an intravascular imaging device that can efficiently traverse physiology within the human body is challenging. In that regard, components at the distal portion of the imaging device can be assembled in a manner that excessively enlarges an outer diameter, which makes navigation through smaller diameter vessels difficult.

Thus, there remains a need for intravascular ultrasound imaging system that overcomes the limitations of a large diameter imaging assembly while achieving efficient assembly and operation.

SUMMARY

Embodiments of the present disclosure provide an improved intravascular ultrasound imaging system for generating images of a blood vessel. A distal portion of an intravascular imaging device can include a flex circuit and a support member around which the flex circuit is positioned. The support member can include conductive portions that are respectively coupled conductors or wires that extend along the length of the intravascular imaging device. For example, conductive material can be positioned on a surface of the support member or within a wall of the support member. The conductive portions of the support member can be electrically connected to a conductive portion of the flex circuit so that the conductors can communicate electrical signals to the flex circuit via the support member. Coupling the conductors to the conductive portion of the support member advantageously allows for the imaging assembly to be assembled with a relatively smaller outer diameter.

In one embodiment, an intravascular imaging device is provided. The intravascular imaging device includes a flexible elongate member sized and shaped for insertion into a vessel of a patient, the flexible elongate member having a proximal portion and a distal portion; an imaging assembly disposed at the distal portion of the flexible elongate member, the imaging assembly including: a flex circuit; a conductor extending along the flexible elongate member and in electrical communication with the flex circuit; and a support member around which the flex circuit is positioned, the support member including a conductive portion electrically coupled to the support member.

In some embodiments, the conductive portion is disposed on a proximal flange of the support member. In some embodiments, the conductive portion extends through a channel formed in the support member. In some embodiments, the flex circuit is in electrical communication with the conductive portion of the support member. In some embodiments, the flex circuit includes a first section having a plurality of transducers, a second section having a plurality of controllers, and a third section having a plurality of conductive traces facilitating communication between the plurality of the transducers and the plurality of controllers. In some embodiments, the conductive portion is in electrical communication with at least one of the plurality of controllers. In some embodiments, the conductive portion is disposed on a surface of the proximal flange. In some embodiments, the conductive portion is disposed within a wall of the proximal flange. In some embodiments, the imaging assembly further comprises a plurality of conductors and wherein the support member includes a plurality of conductive portions. In some embodiments, the plurality of conductors comprises four conductors and the plurality of conductive portions comprises four conductive portions, wherein each one of the plurality of conductors is in communication with a respective one of the plurality of conductive portions. In some embodiments, the plurality of conductive portions are spaced around a circumference of the proximal flange. In some embodiments, the plurality of conductive portions are adjacent to one another. In some embodiments, the device further includes a conductive pad in electrical communication with conductive portion, wherein the conductor is electrically coupled to the conductive pad. In some embodiments, the conductor is soldered to the conductive pad.

In one embodiment, a method of assembling an intravascular imaging device is provided. The method includes obtaining a support member having a conductive portion; positioning a flex circuit around the support member such that the flex circuit is in electrical communication with the conductive portion of the support member; electrically coupling a conductor to the conductive portion of support member such that the conductor is in electrical communication with the flex circuit; and coupling a flexible elongate member to at least one of the flex circuit or the support member such that the flex circuit and the support member are disposed at a distal portion of the flexible elongate member.

In some embodiments, the obtaining includes filling a channel of the support member with a conductive material. In some embodiments, the electrically coupling includes electrically coupling the conductor to a conductive pad disposed on a proximal flange of the support member. In some embodiments, the electrically coupling includes soldering the conductor to the conductive portion of the support member. In some embodiments, the method further includes positioning the conductor within the flexible elongate member. In some embodiments, the support member includes a plurality of conductive portions and wherein the electrically coupling includes electrically coupling each one a plurality of conductors to a respective one of the plurality of conductive portions.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
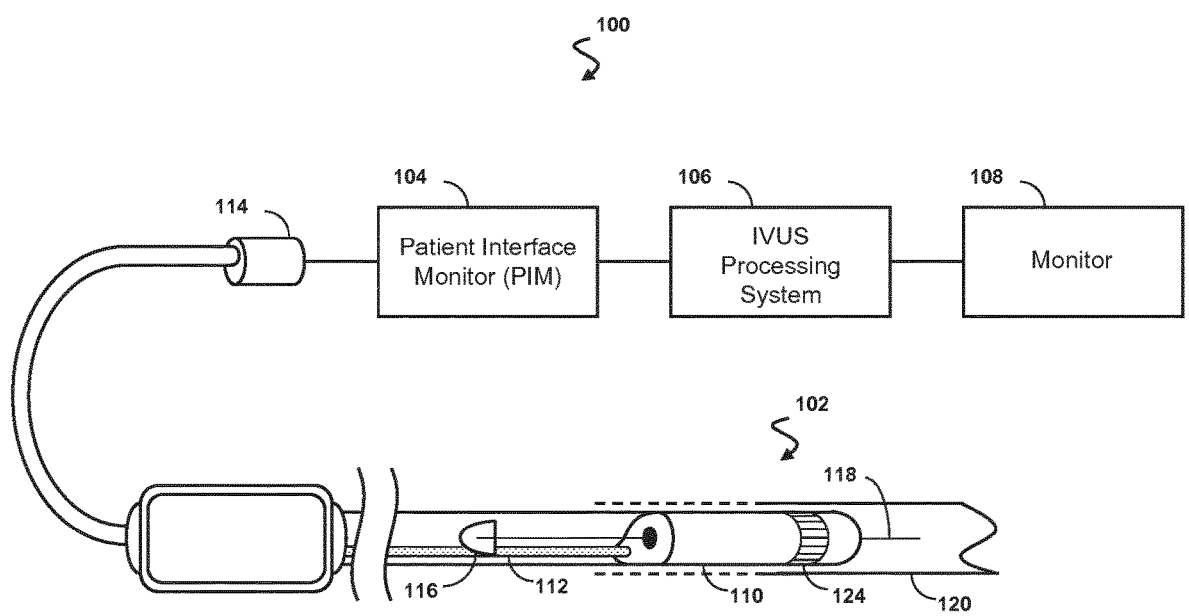
FIG. 1 is a diagrammatic schematic view of an imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the focusing system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intravascular ultrasound (IVUS) imaging system 100, according to aspects of the present disclosure. The IVUS imaging system 100 may include a solid-state IVUS device 102 such as a catheter, guide wire, or guide catheter, a patient interface module (PIM) 104, an IVUS processing system or console 106, and a monitor 108.

At a high level, the IVUS device 102 emits ultrasonic energy from a transducer array 124 included in scanner assembly 110 mounted near a distal end of the catheter device. The ultrasonic energy is reflected by tissue structures in the medium, such as a vessel 120, surrounding the scanner assembly 110, and the ultrasound echo signals are received by the transducer array 124. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s) to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) 126 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and lowvoltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be may be used to examine man-made structures such as, but without limitation, heart valves, stents, shunts, filters and other devices.

Figure 2:
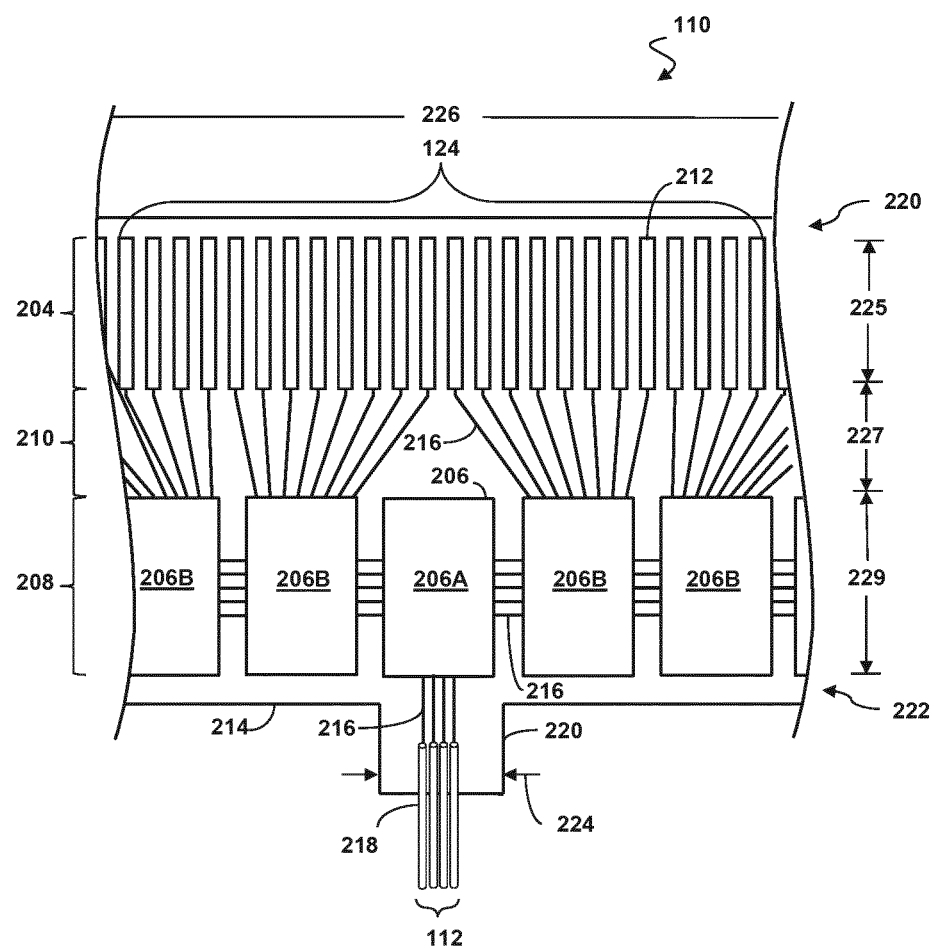
FIG. 2 is a diagrammatic top view of a scanner assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

Figure 3:
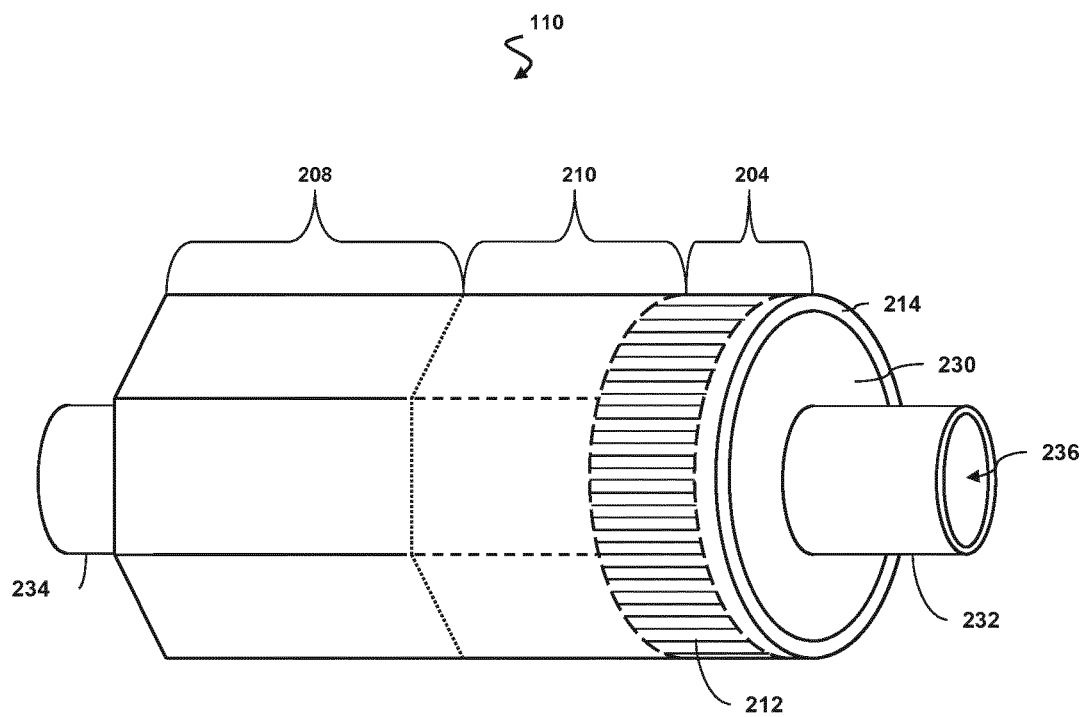
FIG. 3 is a diagrammatic side view of a scanner assembly in a rolled configuration around a support member, according to aspects of the present disclosure.

FIG. 2 is a top view of a portion of an ultrasound scanner assembly 110 according to an embodiment of the present disclosure. The assembly 110 includes a transducer array 124 formed in a transducer region 204 and transducer control logic dies 206 (including dies 206A and 206B) formed in a control region 208, with a transition region 210 disposed therebetween. The transducer control logic dies 206 and the transducers 212 are mounted on a flex circuit 214 that is shown in a flat configuration in FIG. 2. FIG. 3 illustrates a rolled configuration of the flex circuit 214. The transducer array 202 is a non-limiting example of a medical sensor element and/or medical sensor element array. The transducer control logic dies 206 is a non-limiting example of a control circuit. The transducer region 204 is disposed adjacent a distal portion 220 of the flex circuit 214. The control region 208 is disposed adjacent the proximal portion 222 of the flex circuit 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or a length 227 of the transition region 210 can be greater than lengths 225, 229 of the transducer region and controller region, respectively. While the imaging assembly 110 is described as including a flex circuit, it is understood that the transducers and/or controllers may be arranged to form the imaging assembly 110 in other configurations, including those omitting a flex circuit.

The transducer array 124 may include any number and type of ultrasound transducers 212, although for clarity only a limited number of ultrasound transducers are illustrated in FIG. 2. In an embodiment, the transducer array 124 includes 64 individual ultrasound transducers 212. In a further embodiment, the transducer array 124 includes 32 ultrasound transducers 212. Other numbers are both contemplated and provided for. With respect to the types of transducers, in an embodiment, the ultrasound transducers 124 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

The scanner assembly 110 may include various transducer control logic, which in the illustrated embodiment is divided into discrete control logic dies 206. In various examples, the control logic of the scanner assembly 110 performs: decoding control signals sent by the PIM 104 across the cable 112, driving one or more transducers 212 to emit an ultrasonic signal, selecting one or more transducers 212 to receive a reflected echo of the ultrasonic signal, amplifying a signal representing the received echo, and/or transmitting the signal to the PIM across the cable 112. In the illustrated embodiment, a scanner assembly 110 having 64 ultrasound transducers 212 divides the control logic across nine control logic dies 206, of which five are shown in FIG. 2. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

The control logic dies are not necessarily homogenous. In some embodiments, a single controller is designated a master control logic die 206A and contains the communication interface for the cable 112. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

The flex circuit 214, on which the transducer control logic dies 206 and the transducers 212 are mounted, provides structural support and interconnects for electrical coupling. The flex circuit 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In the flat configuration illustrated in FIG. 2, the flex circuit 214 has a generally rectangular shape. As shown and described herein, the flex circuit 214 is configured to be wrapped around a support member 230 (FIG. 3) to form a cylindrical toroid in some instances. Therefore, the thickness of the film layer of the flex circuit 214 is generally related to the degree of curvature in the final assembled scanner assembly 110. In some embodiments, the film layer is between 5 µm and 100 µm, with some particular embodiments being between 12.7 µm and 25.1 µm.

To electrically interconnect the control logic dies 206 and the transducers 212, in an embodiment, the flex circuit 214 further includes conductive traces 216 formed on the film layer that carry signals between the control logic dies 206 and the transducers 212. In particular, the conductive traces 216 providing communication between the control logic dies 206 and the transducers 212 extend along the flex circuit 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flex circuit 214. Suitable materials for the conductive traces 216 include copper, gold, aluminum, silver, tantalum, nickel, and tin, and may be deposited on the flex circuit 214 by processes such as sputtering, plating, and etching. In an embodiment, the flex circuit 214 includes a chromium adhesion layer. The width and thickness of the conductive traces 216 are selected to provide proper conductivity and resilience when the flex circuit 214 is rolled. In that regard, an exemplary range for the thickness of a conductive trace 216 and/or conductive pad is between 10-50 µm. For example, in an embodiment, 20 µm conductive traces 216 are separated by 20 µm of space. The width of a conductive trace 216 on the flex circuit 214 may be further determined by the width of the conductor 218 to be coupled to the trace/pad.

The flex circuit 214 can include a conductor interface 220 in some embodiments. The conductor interface 220 can be a location of the flex circuit 214 where the conductors 218 of the cable 114 are coupled to the flex circuit 214. For example, the bare conductors of the cable 114 are electrically coupled to the flex circuit 214 at the conductor interface 220. The conductor interface 220 can be tab extending from the main body of flex circuit 214. In that regard, the main body of the flex circuit 214 can refer collectively to the transducer region 204, controller region 208, and the transition region 210. In the illustrated embodiment, the conductor interface 220 extends from the proximal portion 222 of the flex circuit 214. In other embodiments, the conductor interface 220 is positioned at other parts of the flex circuit 214, such as the distal portion 220, or the flex circuit 214 omits the conductor interface 220. A value of a dimension of the tab or conductor interface 220, such as a width 224, can be less than the value of a dimension of the main body of the flex circuit 214, such as a width 226. In some embodiments, the substrate forming the conductor interface 220 is made of the same material(s) and/or is similarly flexible as the flex circuit 214. In other embodiments, the conductor interface 220 is made of different materials and/or is comparatively more rigid than the flex circuit 214. For example, the conductor interface 220 can be made of a plastic, thermoplastic, polymer, hard polymer, etc., including polyoxymethylene (e.g., DELRIN®), polyether ether ketone (PEEK), nylon, and/or other suitable materials. As described in greater detail herein, the support member 230, the flex circuit 214, the conductor interface 220 and/or the conductor(s) 218 can be variously configured to facilitate efficient manufacturing and operation of the scanner assembly 110.

Figure 4:
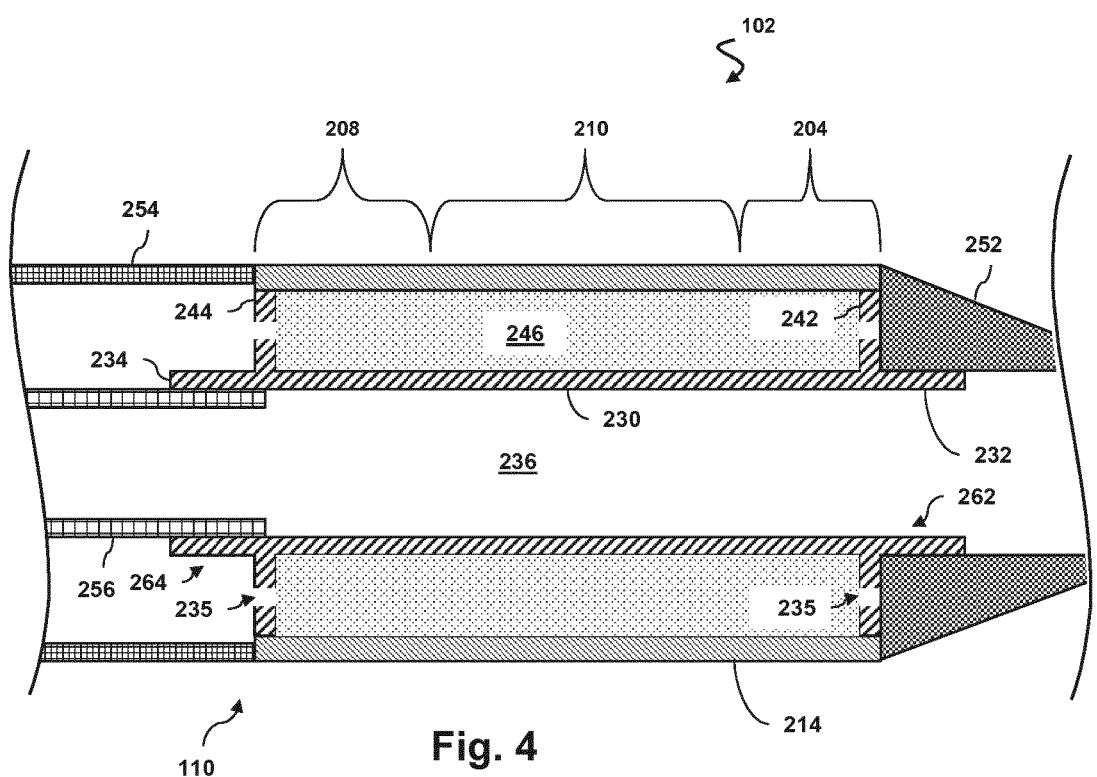
FIG. 4 is a diagrammatic cross-sectional side view of a distal portion of an intravascular device, according to aspects of the present disclosure.

In some instances, the scanner assembly 110 is transitioned from a flat configuration (FIG. 2) to a rolled or more cylindrical configuration (FIGS. 3 and 4). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

As shown in FIGS. 3 and 4, the flex circuit 214 is positioned around the support member 230 in the rolled configuration. FIG. 3 is a diagrammatic side view with the flex circuit 214 in the rolled configuration around the support member 230, according to aspects of the present disclosure. FIG. 4 is a diagrammatic cross-sectional side view of a distal portion of the intravascular device 110, including the flex circuit 214 and the support member 230, according to aspects of the present disclosure.

The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending longitudinally therethrough. The lumen 236 is in communication with the exit port 116 and is sized and shaped to receive the guide wire 118 (FIG. 1). The support member 230 can be manufactured accordingly to any suitable process. For example, the support member 230 can be machined, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another.

Stands 242, 244 that extend vertically are provided at the distal and proximal portions 262, 264, respectively, of the support member 230. The stands 242, 244 elevate and support the distal and proximal portions of the flex circuit 214. In that regard, portions of the flex circuit 214, such as the transducer portion 204, can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244. To improve acoustic performance, any cavities between the flex circuit 214 and the surface of the support member 230 are filled with a backing material 246. The liquid backing material 246 can be introduced between the flex circuit 214 and the support member 230 via passageways 235 in the stands 242, 244. In some embodiments, suction can be applied via the passageways 235 of one of the stands 242, 244, while the liquid backing material 246 is fed between the flex circuit 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flex circuit 214.

The support member 230 can be substantially cylindrical in some embodiments. Other shapes of the support member 230 are also contemplated including geometrical, non-geometrical, symmetrical, non-symmetrical, cross-sectional profiles. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can be flexible elongate member that extend from proximal portion of the intravascular 102, such as the proximal connector 114, to the imaging assembly 110. For example, the proximal inner member 256 can be received within a proximal flange 234. The proximal outer member 254 abuts and is in contact with the flex circuit 214. A distal member 252 is coupled to the distal portion 262 of the support member 230. The distal member 252 can be a flexible component that defines a distal most portion of the intravascular device 102. For example, the distal member 252 is positioned around the distal flange 232. The distal member 252 can abut and be in contact with the flex circuit 214 and the stand 242. The distal member 252 can be the distal-most component of the intravascular device 102.

One or more adhesives can be disposed between various components at the distal portion of the intravascular device 102. For example, one or more of the flex circuit 214, the support member 230, the distal member 252, the proximal inner member 256, and/or the proximal outer member 254 can be coupled to one another via an adhesive.

Figure 5:
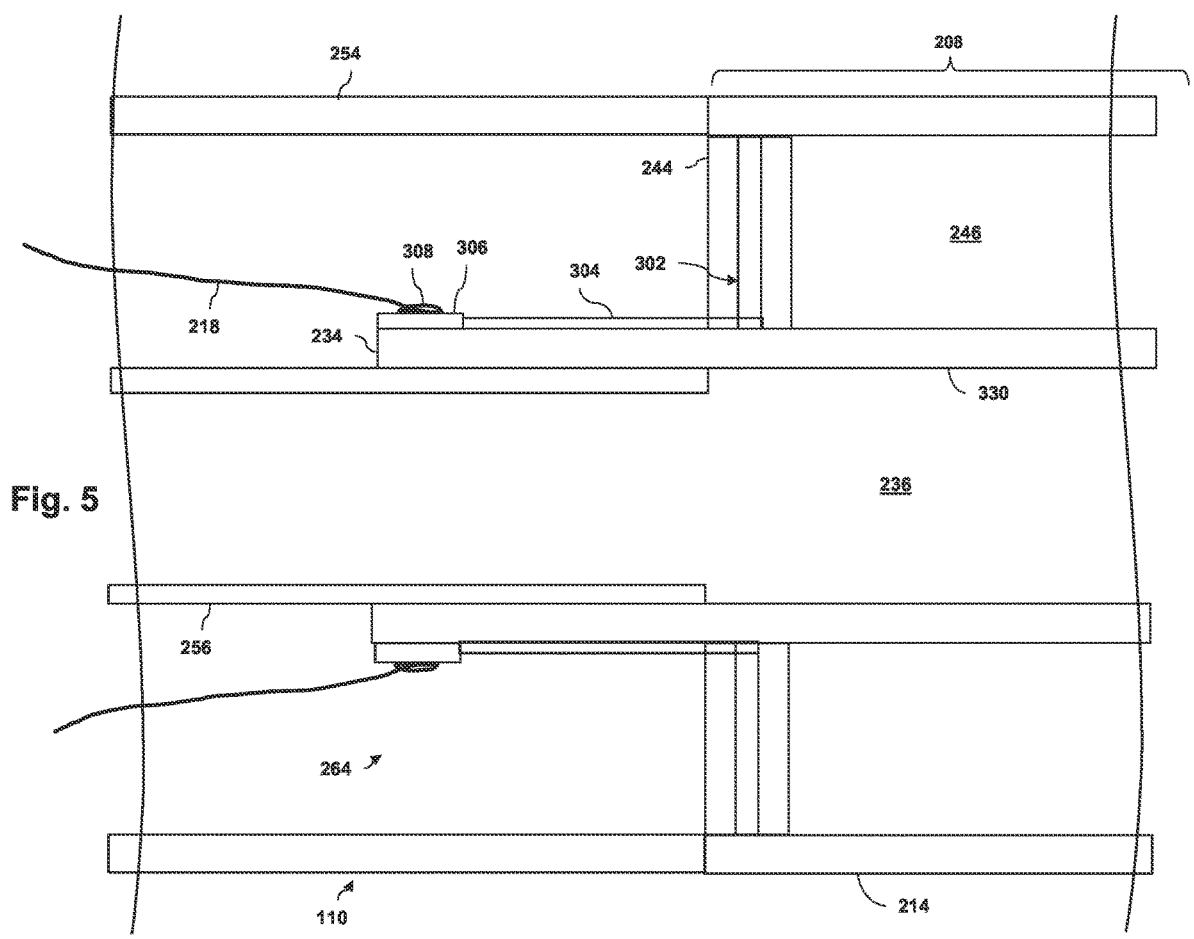
FIG. 5 is a diagrammatic cross-sectional side view of a proximal portion of an imaging assembly of an intravascular device, according to aspects of the present disclosure.

FIG. 5 is diagrammatic cross-sectional side view of a proximal portion of the imaging assembly 110 of an intravascular device. FIG. 5 is illustrates an embodiment of a support member 330 including one or more conductive portions 304, 306. The support member 330 can be similar to the support member 230 in some aspects. The support member 330 additionally includes the conductive portion(s) 304, 306 facilitate electrical communication between the conductors 218 of the cable 112 (FIGS. 1 and 2) and the flex circuit 214. In that regard, the conductors 214 may be electrically and/or mechanically coupled to conductive portion(s) 304, 306 of the support member 230, rather than electrically and/or mechanically coupled to the interface 220 of the flex circuit 214 (FIG. 2).

Electrically coupling the conductive member 218 to the support member 330, rather than the flex circuit 214, can advantageously minimize the outer diameter of the imaging assembly 110. In some instances, the outer diameter of the imaging assembly can undesirably bulge in the area where the conductors 218 are coupled to the conductor interface 220 (FIG. 2). Aspects of the present disclosure address this difficulty by establishing electrical communication between the flex circuit 214 and the conductors 218 within an interior of the imaging assembly 110, at the support member 330. The outer diameter of the imaging assembly can also be undesirably large if the conductors 218 extend along an exterior surface of the outer member 254 after being coupled to the conductor interface 220. Because the conductors 218 are coupled to the support member 230 within the interior of the imaging assembly 110, according to aspects of the present disclosure, the conductors 218 can extend along a length of the intravascular device within, e.g., the outer member 254. A more robust electrical and/or mechanical connection can also be established between the conductors 218 and the support member 330, which is relatively more rigid than the flex circuit 214.

A conductive portion 304 of the support member 330 is a channel 302 filled with a conductive material 304. In the embodiment of FIG. 5, the channel 302 extends within a wall of the stand 244 and along a surface of the proximal flange 234. It is understood that the conductive portion 304 can positioned anywhere within and/or along a surface of the support member 330. The channel 302 can be formed according to any suitable process, including machining the support member 330 to form the channel 302 and/or molding along support member 330 with the channel 302 formed therein. Similarly, the channel 302 can be filled according to any suitable process, such as a physical vapor deposition, chemical vapor deposition, chemical adsorption, physical adsorption, dip coating, solvent evaporation, among others. In some embodiments, the conductive material is a metal, such as gold, silver, copper, aluminum, steel, and/or other suitable materials.

The conductive portion 304 is in electrical contact with the flex circuit 208. For example, the conductive portion 304 may be communication with electronic components of the flex circuit 214, such as the controllers 206A, 206B, transducers 212, and/or conductive traces 215. An inferior or bottom side of the flex circuit 214 (e.g., the side of the flex circuit 214 in contact with the support member 330) can have a conductive portion that physically contacts the conductive portion 304 within the stand 244 of the support member 330 when the flex circuit 214 is positioned around the support member 330. In that regard, the flex circuit 214 and the support member 330 may be aligned such that the conductive portion of the flex circuit 214 and the conductive portion 304 are in contact. An adhesive may be used to affix the flex circuit 214 and the support member 330.

The conductive portion 304 may extend along a surface of the proximal flange 234. In some embodiments, the conductor 218 is electrically coupled directly to the conductive portion 304. In other embodiments, as illustrated in FIG. 5, the conductor 218 is electrically coupled directly to a conductive pad 306. For example, as shown, solder 308 may be used to electrically and/or mechanically The conductive pad 306 may be conductive region of the support member 330 that is configured to allow the conductors the be efficiently coupled thereto. For example, the conductive pad 306 may be sized and shaped to so that a user, during manufacturing, can quickly and easily solder the conductor 218 to the support member 330. For example, the length, width, and/or height of the conductive pad 306 may be larger than corresponding dimensions of the conductive portion 304. The conductive portion 304 may be in contact with and electrically coupled to the conductive pad 306. The conductor 218 may be in electrical communication with the conductive portion 304 via the conductive pad 306.

The conductors 218 extend between the proximal connector 114 and the imaging assembly 110 along the length of and within an interior of the intravascular device 102 (FIG. 1). For example, the conductors can be disposed within a lumen of the outer member 254, such as between the inner member 256 and the outer member 254.

Figure 6:
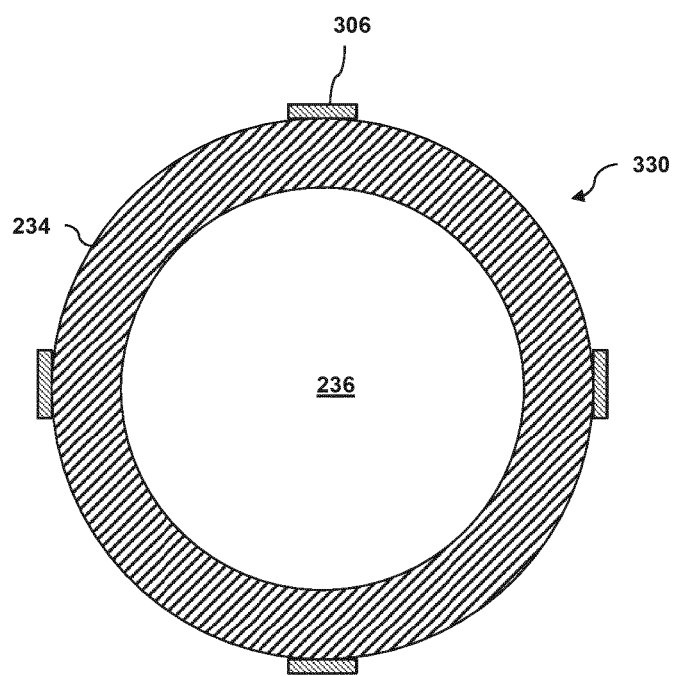
FIG. 6 is a diagrammatic end view of a proximal portion of a support member, according to aspects of the present disclosure.

Any suitable number of conductors 218 can be electrically coupled the support member 330. The support member 330 can include a corresponding number of conductive portions 304, 306 based on the number of conductors 218. For example, one, two, three, four, five, six, seven, or more conductors 218 can extend along the length of the intravascular device. The support member can correspondingly include one, two, three, four, five, six, seven, or more conductive portions 304, 306. Two sets of conductive portions 304, 306 are shown in the cross-sectional illustration of FIG. 5. FIG. 6 is a diagrammatic end view of the proximal portion 264 of the support member 330 that includes four conductive portions 306 disposed on the proximal flange 234. Each one of four conductors 218 can be electrically and/or mechanically coupled to a respective one of the four conductive pads 306 of the support member 330.

Figure 7:
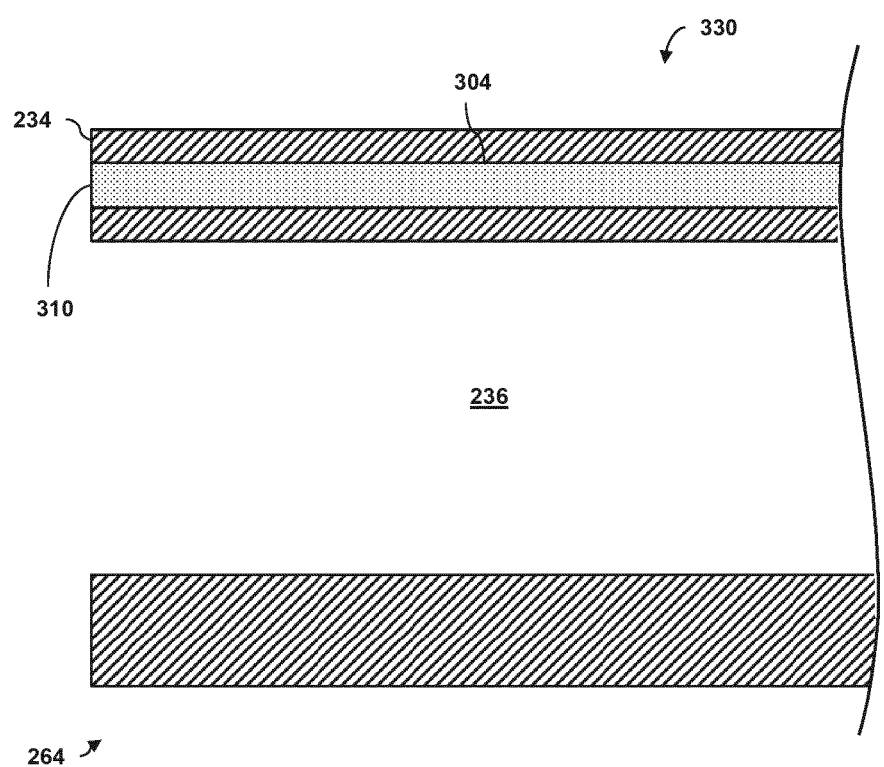
FIG. 7 is a diagrammatic cross-sectional side view of a proximal portion of an imaging assembly of the intravascular device of, according to aspects of the present disclosure.
Figure 8:
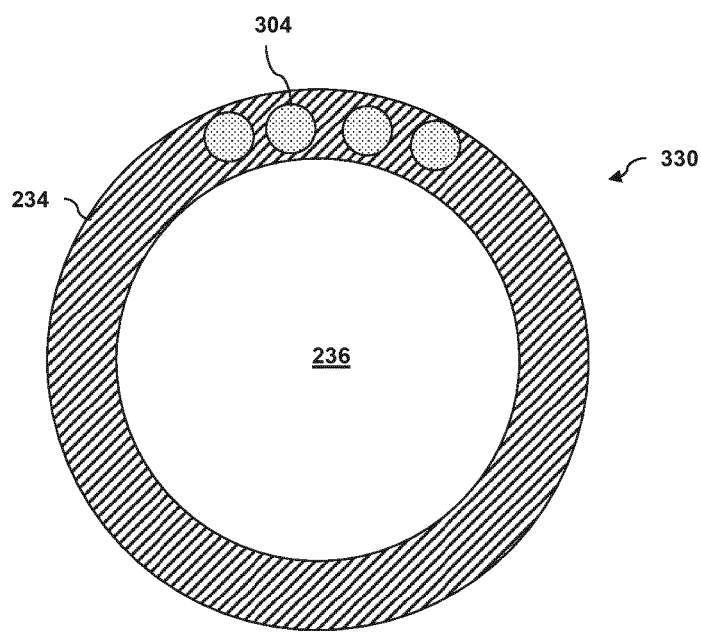
FIG. 8 is a diagrammatic end view of a proximal portion of a support member, according to aspects of the present disclosure.

FIGS. 7 and 8 illustrate an embodiment of the support member 330 that includes the conductive portion 304 extending within a wall of the proximal flange 234. FIG. 7 diagrammatic cross-sectional side view of the proximal portion 264 of the support member 330, including the proximal flange 234. FIG. 8 is a diagrammatic end view of the proximal portion 264 of the support member 330, including the proximal flange 234. The conductive portion 304 is disposed within the proximal flange 234 in a similar manner as the conductive portion 304 is disposed within the stand 244 (FIG. 5). Accordingly, the conductive portion 304 can extend entirely through the structure of the support member 330, rather than along a surface of the support member 330, in some embodiments. The conductor 218 can be electrically and/or mechanically coupled to the conductive portion 304 at a proximal end 310. In some embodiments, the proximal flange 234 can include a recess at the distal end 310 that receives the conductor 218. For example, the conductor 218 can be positioned within and coupled to the conductive portion 304 within a wall of the proximal flange 234. While the conductor 218 is directly coupled to the conductive portion 304 in the illustrated embodiment, other embodiments of the support member 330 can include a conductive pad 306 (FIGS. 5 and 6) in communication with the conductive portion 304 and directly coupled to the conductor 218.

As shown in FIGS. 6 and 8, the conductive portions 304, 306 can be variously positioned around circumference of the proximal flange 234. FIG. 6 illustrates the conductive pads 306 spaced around the circumstance of the proximal flange 234. In that regard, the conductive pads 306 are equally spaced around circumference of the proximal flange 234, within each conductive pad 306 positioned in a quadrant of the circumference. Equally spacing the conductive pads 306 may allow a user to individually couple the conductor 218 to the respective conductive pad 306 such that the electrical and/or mechanical connection is effectively established. Spacing between the conductive pads 306 may also ensure the conductors 218 remain electrically isolated. Distributing the conductive pads 306 around the circumference of the proximal flange 234 may also result in the positioning conductive portions 304 around the circumference of the support member 330. For example, as shown in FIG. 5, the conductive portions 304 are shown on both the superior/top and inferior/bottom portions of the stand 244 and the proximal flange 234.

FIG. 8 illustrates the conductive portions 304 are positioned adjacent to one another. In that regard, the grouping of the multiple conductive portions 304 can be disposed anywhere along the circumference of the proximal flange 234, including in the superior or top section shown in FIG. 8. Positioning the multiple conductive portions 304 in a relatively small area may allow for the conductors 218 to be coupled to support member 330 in an efficient manner while ensuring the conductors 218 are electrically isolated. Relatively less spacing between the conductive portions 304 may also result in conductive portions 304 being positioned in fewer areas around the support member 330. For example, as shown in FIG. 7, the conductive portions 304 are shown only on the superior/top portion of the proximal flange 234.

Figure 9:
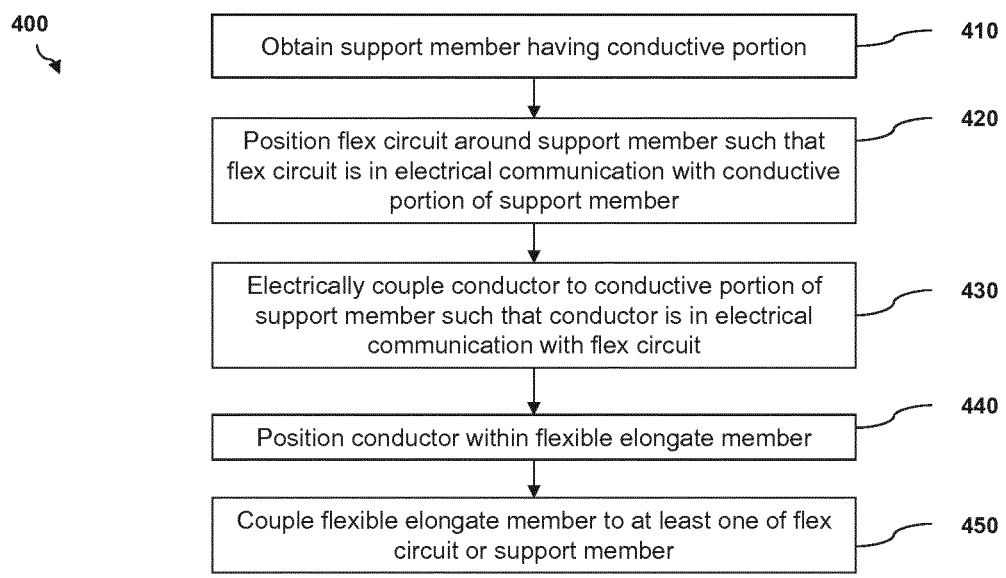
FIG. 9 is a flow diagram of a method of assembling an intravascular device, according to aspects of the present disclosure.

FIG. 9 is a flow diagram of a method 400 of assembling an intravascular imaging device, including an imaging assembly with a support member described herein. It is understood that the steps of method 400 may be performed in a different order than shown in FIG. 9, additional steps can be provided before, during, and after the steps, and/or some of the steps described can be replaced or eliminated in other embodiments. The steps of the method 400 can be carried out by a manufacturer of the intravascular imaging device.

At step 410, the method 410 includes obtaining a support member. The support member includes a conductive portion. For example, the conductive portion may extend along a surface or a within a wall of the support member. In some embodiments, a proximal portion of the support member, such as a proximal flange, includes the conductive portion. In some embodiments, step 410 can include filling a channel of the support member with a conductive material.

At step 420, the method 400 includes positioning a flex circuit around a support member to form an imaging assembly of the intravascular device. The flex circuit can include a conductive portion that contacts and establishes electrical communication with the conductive portion of the support member when the flex circuit is positioned around the support member. Step 420 can include aligning the flex circuit and the support member such that the respective conductive portions contact when the flex circuit is positioned around the support member.

At step 430, the method 400 includes electrically coupling a conductor to the conductive portion of the support member. As a result, the conductor is in electrical communication with the flex circuit. For example, the flex circuit can include a first section having a plurality of transducers, a second section having a plurality of controllers, and a third section having a plurality of conductive traces facilitating communication between the plurality of the transducers and the plurality of controllers. At step 430, the conductor establishes electrical communication with the controller(s), transducer(s), and/or conductive traces of flex circuit. Electrical signals representative of control signals to the controller(s), imaging data from the transducer(s), and/or other suitable data are transmitted to/from the conductors to the flex circuit via the conductive portion of the support member. In some embodiments, step 430 can include electrically coupling the conductor to a conductive pad disposed on a proximal flange of the support member. In some embodiments, step 430 can include soldering the conductor to the conductive portion of the support member. In some embodiments, the support member includes a plurality of conductive portions. The intravascular device can include a plurality of conductors. In such embodiments, step 430 includes electrically coupling each one a plurality of conductors to a respective one of the plurality of conductive portions.

At step 440, the method 400 includes positioning the one or more conductors within a flexible elongate member. At step 440, the method 400 can include coupling the flex circuit and/or the support member to one or more flexible elongate members. For example, one or more proximal flexible elongate members (e.g., an inner member and/or an outer member) are coupled to the flex circuit and/or the support member. In that regard, the flex circuit and/or the support member are positioned at the distal portion of the flexible elongate member. The conductor(s) can extend along a length of the intravascular device. The conductor(s) can be threaded through the flex elongate member such that, e.g., the conductor(s) are positioned with a lumen of an outer member and/or disposed between an inner member and an outer member.

The method 400 can also include coupling the flex circuit and/or the support member to a distal component that defines a distal-most end of the intravascular imaging device. The method 400 can include introducing adhesive to affix the flex circuit and the support member and/or other components of the intravascular imaging device. The method 400 can also include introducing a liquid acoustic backing material between the flex circuit and the support member. A mandrel can be temporarily positioned around the support member to allow positioning of the flex circuit around the support member. The method 400 can also include removing the mandrel after the liquid acoustic backing material has cured.

Various embodiments of an intravascular device and/or imaging assembly can include features described in U.S. Provisional App. No. 62/315,395, filed Mar. 30, 2016, U.S. Provisional App. No. 62/315,406, filed Mar. 30, 2016, U.S. Provisional App. No. 62/315,428, filed Mar. 30, 2016, and U.S. Provisional App. No. 62/315,416, filed Mar. 30, 2016, the entireties of which are hereby incorporated by reference herein.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular imaging device comprising:
   a flexible elongate member sized and shaped for insertion into a vessel of a patient, the flexible elongate member comprising a proximal portion and a distal portion;
   an imaging assembly disposed at the distal portion of the flexible elongate member, the imaging assembly including:
      a flex circuit comprising a flexible material;
      a conductor extending along the flexible elongate member and in electrical communication with the flex circuit; and
      a support member including a first segment with a first diameter and a second segment with a second diameter greater than the first diameter, wherein the support member further includes a first conductive portion electrically coupled to the conductor and the flex circuit to transmit an electrical signal between the conductor and the flex circuit, wherein at least part of the first conductive portion is positioned outside of at least one of the first segment or the second segment, wherein the flexible material is wrapped around the support member such that a second conductive portion of the flex circuit contacts and establishes electrical communication with the first conductive portion.

2. The device of claim 1, wherein the first conductive portion is disposed on a proximal flange of the support member, wherein the first segment comprises the proximal flange.

3. The device of claim 1, wherein the first conductive portion extends through a channel formed in the support member.

4. The device of claim 1, wherein the flex circuit includes a first section comprising a plurality of transducers, a second section comprising a plurality of controllers, and a third section comprising a plurality of conductive traces facilitating communication between the plurality of the transducers and the plurality of controllers.

5. The device of claim 4, wherein the first conductive portion is in electrical communication with at least one of the plurality of controllers.

6. The device of claim 2, wherein the first conductive portion is disposed on a surface of the proximal flange.

7. The device of claim 2, wherein the first conductive portion is disposed within a wall of the proximal flange.

8. The device of claim 2, wherein the imaging assembly further comprises a plurality of conductors and wherein the support member includes a plurality of first conductive portions.

9. The device of claim 8, wherein the plurality of conductors comprises four conductors and the plurality of first conductive portions comprises four conductive portions, wherein each one of the plurality of conductors is in communication with a respective one of the plurality of first conductive portions.

10. The device of claim 9, wherein the plurality of first conductive portions are spaced around a circumference of the proximal flange.

11. The device of claim 9, wherein the plurality of first conductive portions are adjacent to one another.

12. The device of claim 1, further comprising a conductive pad in electrical communication with the first conductive portion, wherein the conductor is electrically coupled to the conductive pad.

13. The device of claim 12, wherein the conductor is soldered to the conductive pad.

14. A method of assembling an intravascular imaging device, the method comprising:
   obtaining a support member comprising:
      a first segment with a first diameter;
      a second segment with a second diameter greater than the first diameter; and
      a first conductive portion, wherein at least part of the first conductive portion is positioned outside of at least one of the first segment or the second segment;
   wrapping a flexible material of a flex circuit around the support member such that a second conductive portion of the flex circuit contacts and establishes electrical communication with the first conductive portion;
   electrically coupling a conductor to the first conductive portion of the support member such that the conductor is in electrical communication with the flex circuit via the first conductive portion; and
   coupling a flexible elongate member to at least one of the flex circuit or the support member such that the flex circuit and the support member are disposed at a distal portion of the flexible elongate member.

15. The method of claim 14, wherein the obtaining includes:
   filling a channel of the support member with a conductive material.

16. The method of claim 14, wherein the electrically coupling includes electrically coupling the conductor to a conductive pad disposed on a proximal flange of the support member.

17. The method of claim 14, wherein the electrically coupling includes soldering the conductor to the first conductive portion of the support member.

18. The method of claim 14, further comprising:
   positioning the conductor within the flexible elongate member.

19. The method of claim 14, wherein the support member includes a plurality of first conductive portions and wherein the electrically coupling includes electrically coupling each of a plurality of conductors to a respective one of the plurality of first conductive portions.

20. The device of claim 1, wherein at least part of the first conductive portion is positioned inside of at least one of the first segment or the second segment.

* * * * *